United States Patent [19]

White

[11] Patent Number: 5,760,095
[45] Date of Patent: Jun. 2, 1998

[54] METHOD AND SYSTEM FOR EFFECTING WITHDRAWAL FROM CAFFEINE DEPENDENCY

[76] Inventor: Hebron B. White, 3093 E. Louise Ave., Salt Lake City, Utah 84109

[21] Appl. No.: 566,067

[22] Filed: Dec. 1, 1995

[51] Int. Cl.[6] .................................. A01N 43/90
[52] U.S. Cl. .................. 514/810; 436/901; 206/531; 206/532
[58] Field of Search .................. 436/901; 514/810, 514/264, 568; 206/531, 532

[56] References Cited

U.S. PATENT DOCUMENTS

| | | | |
|---|---|---|---|
| 3,759,371 | 9/1973 | Marks | 206/531 |
| 4,486,436 | 12/1984 | Sunshine et al. | 514/263 |
| 4,777,174 | 10/1988 | Sunshine et al. | 514/264 |
| 5,051,426 | 9/1991 | Parnell | 514/263 |
| 5,219,858 | 6/1993 | Parnell | 514/264 |

OTHER PUBLICATIONS

Goldstein, A., Addiction: From Biology to Drug Policy, Freeman and Company, 1994, pp. 187 and 215–217.

*Primary Examiner*—C. Warren Ivy
*Assistant Examiner*—Garth M. Dahlen

[57] ABSTRACT

A method and system for effecting withdrawal from caffeine dependency is disclosed wherein the system comprises a regiment of dosage units having varying proportions of caffeine and an analgesic. One embodiment utilizes a first dosage unit which has a caffeine content equivalent to the daily caffeine intake of the individual. This level of caffeine is reduced while the level of analgesia is increased. The relevant proportion of caffeine is gradually decreased until the individual is no longer ingesting caffeine. In some embodiments, a placebo is administered during the final stages of method and system.

13 Claims, 6 Drawing Sheets

METHOD AND SYSTEM FOR EFFECTING WITHDRAWAL FROM CAFFEINE DEPENDENCY

BACKGROUND OF THE INVENTION

1. The Field of the Invention

The present invention relates to a system to be used by persons who have a history of prescribed or habitual caffeine use. In particular, the invention relates to compositions and methods for accomplishing withdrawal from dependency on caffeine while at the same time minimizing or preventing the inherent side effects of caffeine withdrawal.

2. The Relevant Technology

It is well known that caffeine is incorporated into a number of substances, foods and beverages regularly ingested by persons for a number of reasons. For example, chocolates and other sweets or candies often contain low levels of caffeine. When ingested over a period of time at regular intervals, a craving for the sweet can occur. The craving is believed by many to be caffeine-related.

Other persons consume regular or large amounts of beverages or soft drinks containing caffeine. It is well recognized that coffee, teas and many soft drinks contain high levels of caffeine.

In addition, caffeine is used medicinally as a stimulant and/or diuretic. For example, caffeine is sometimes prescribed in large doses for persons having severe hay fever allergies. Small doses of caffeine are also used as a stimulant to enhance or accelerate the effect of other drugs. Examples of these uses can be found in U.S. Pat. Nos. 5,219,858; 4,777,174; and 4,486,436.

If the quantity of caffeine is sufficiently high and ingested over a regular and long enough period of time, individuals can become accustomed to the caffeine effects and indeed have cravings for caffeine in the form of a dependency or addiction. Such compulsive physiological habits or needs for a given substance are difficult and often painful to overcome.

Physiological addictions, including dependence upon caffeine, can be overcome. A common technique is an immediate and total denial of any caffeine. In either case this weaning is usually accompanied by mild to severe side effects. For example, withdrawal from a caffeine addiction often results in severe headaches or migraines. Indeed, many persons do not attempt caffeine withdrawal because of the known side effects. What is needed are compositions and methods which permit a caffeine-dependent individual to be weaned of caffeine and at the same time provide physiologic and psychologic assistance to lessen or even avoid the often excruciating headaches associated with caffeine withdrawal.

SUMMARY AND OBJECTS OF THE INVENTION

The present invention is directed to a system which assists persons in discontinuing the intake of caffeine over time by lessening the suffering or anticipated suffering of the side effects from withdrawal. In particular, the present invention is directed to a system utilizing dosage regimens which physiologically and psychologically assist persons in weaning themselves of caffeine dependency by incrementally decreasing caffeine intake while concomitantly increasing analgesia to counteract the side effects of caffeine withdrawal.

The present invention is directed to a system utilizing a dosage regimen in which the caffeine-to-analgesia ratio by weight begins at 100%:0% and over time transitions to 0%:100%. In the preferred embodiment, the percentage weight ratio would ultimately go to 0%:0% where the person at the last stages, for psychological reasons, is merely taking a placebo.

The dosage form contemplated by the present invention would be embodied in a single dosage unit or tablet. As a result, the present invention contemplates providing the patient a plurality of dosage units or tablets taken in a predetermined order or dosage regimen such that the dosage units contain varying percentage weight ratios of caffeine and an analgesic such that over time the amount of caffeine received by the person is decreased and the amount of analgesic is increased.

One preferred embodiment of the system utilizes a stiff card within which the tablets are presented in a preselected designated order or regimen. The user merely pushes the tablet through the wrapping of the card to dispense the next dose. The tablets are arranged to provide the desired ratio of caffeine to analgesia.

It is, therefore, an object of the present invention to assist persons desiring to withdraw from caffeine dependency.

It is also an object of this invention to provide a system utilizing a regimen of predetermined dosages of caffeine over a temporal period such that the caffeine intake of the person is decreased over time.

It is a still further object of the present invention to provide an increasing dosage of analgesic for persons withdrawing from caffeine to counteract common side effects of caffeine withdrawal.

Another object of the present invention is to provide a system for withdrawal from caffeine dependency that reduces suffering the common side effects of caffeine withdrawal by providing a predetermined dosage regimen of a combination of decreasing amounts of caffeine and increasing amounts of analgesic.

It is also an object of the present invention to provide a system for caffeine withdrawal which has the psychological benefit of aiding in the withdrawal from caffeine by assisting the person to avoid experiencing the common side effects of headaches.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
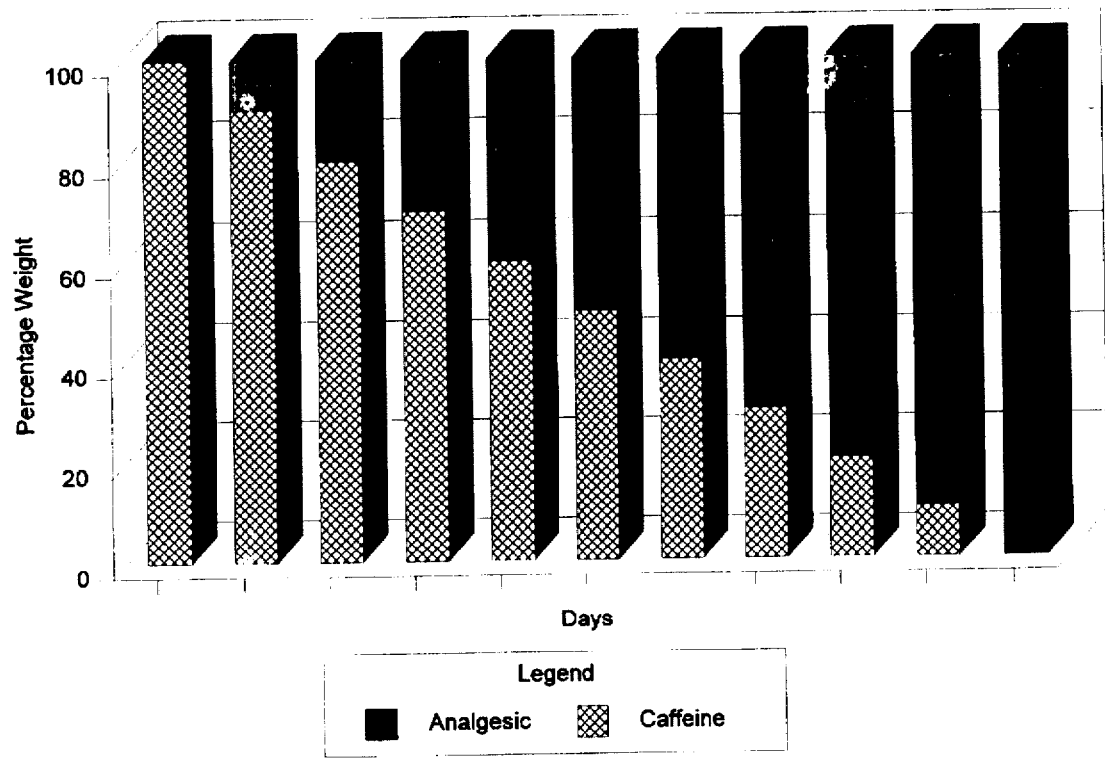
FIG. 1 depicts the relative proportions of caffeine and an analgesic in dosage units administered over time in one embodiment of the system.

The present invention is directed to a system for effecting withdrawal from caffeine dependency to assist persons in withdrawing from caffeine by reducing the suffering of the inherent side effects of withdrawal. The present invention utilizes at least two components which assist in caffeine withdrawal. The first, a psychological component, through predetermined and preformulated compositions, ensures that the patient does not suffer headaches or other side effects of caffeine withdrawal. As a result, the person is psychologically motivated and encouraged by being able to withdraw from caffeine without suffering the usually attendant physical pain of doing so.

A second component is the medicinal component which accomplishes a physiological withdrawal from caffeine dependency over a period of time. This physiological component utilizes a series of dosage units having at least two elements, namely caffeine and a quantity of analgesic taken over a previously determined dosage regimen. Some embodiments utilize an increasing quantity of excipient such as when the dosage unit is utilized as a placebo.

The system of the present invention comprise varying amounts of caffeine and analgesic in a dosage regimen, and in some embodiments, a placebo in place of the combined quantities of caffeine and analgesic at the end of the dosage regimen.

The present invention utilizes a series of dosage units or tablets. Over time, the composition of each dosage unit varies in its quantity of caffeine compared to its quantity of analgesic and/or other ingredients. For example, FIGS. 1–6 indicate a beginning or initial quantity of caffeine present in a dosage unit at day 0 or day 1. Subsequent thereto, as shown in FIGS. 1–6, the percentage weight of caffeine is decreased. FIGS. 1–4 represent a substantially linear decrease in the caffeine quantity. However, the present invention also contemplates a nonlinear decrease in the quantity of caffeine depending upon the nature of the user's dependency, see FIGS. 5–6. However, for the purposes of presentation, most of the discussion herein will assume a substantially linear decrease in the amount of caffeine. At least one embodiment illustrates a regime having plateaus, FIG. 6.

Caffeine dependency can range in degree. For example, persons who suffer conditions such as severe allergies may have been taking amounts of caffeine up to hundreds of milligrams per day. Heavy coffee drinkers may have accustomed themselves to similar levels of caffeine. As a result, in order to provide the psychological benefit of not experiencing the side effects of caffeine withdrawal, the initial dosage unit contemplated by the present invention meets or exceeds the level of caffeine dependency of the person. In one embodiment represented by FIG. 4, the initial quantity of caffeine in the dosage unit remains at or above the level to which the person is accustomed for the first few days. In so doing, the patient experiences no side effects whatsoever because, in fact, the withdrawal has not yet begun. However, this provides the psychological advantage of encouraging the person to continue with the regimen as it is thus far not subjecting the person to the common side effects of headache.

The initial quantity of caffeine in the unit dose could begin at one hundred milligrams and taper off. In other embodiments the initial quantity of caffeine could be hundreds or many hundreds of milligrams of caffeine depending upon the amount to which the person is accustomed. Then, whether that dosage is maintained for a period of time as shown in FIGS. 2–6, or whether a decreasing caffeine amount proceeds immediately as shown in FIG. 1, the amount of caffeine user is not radically reduced at first.

Figure 2:
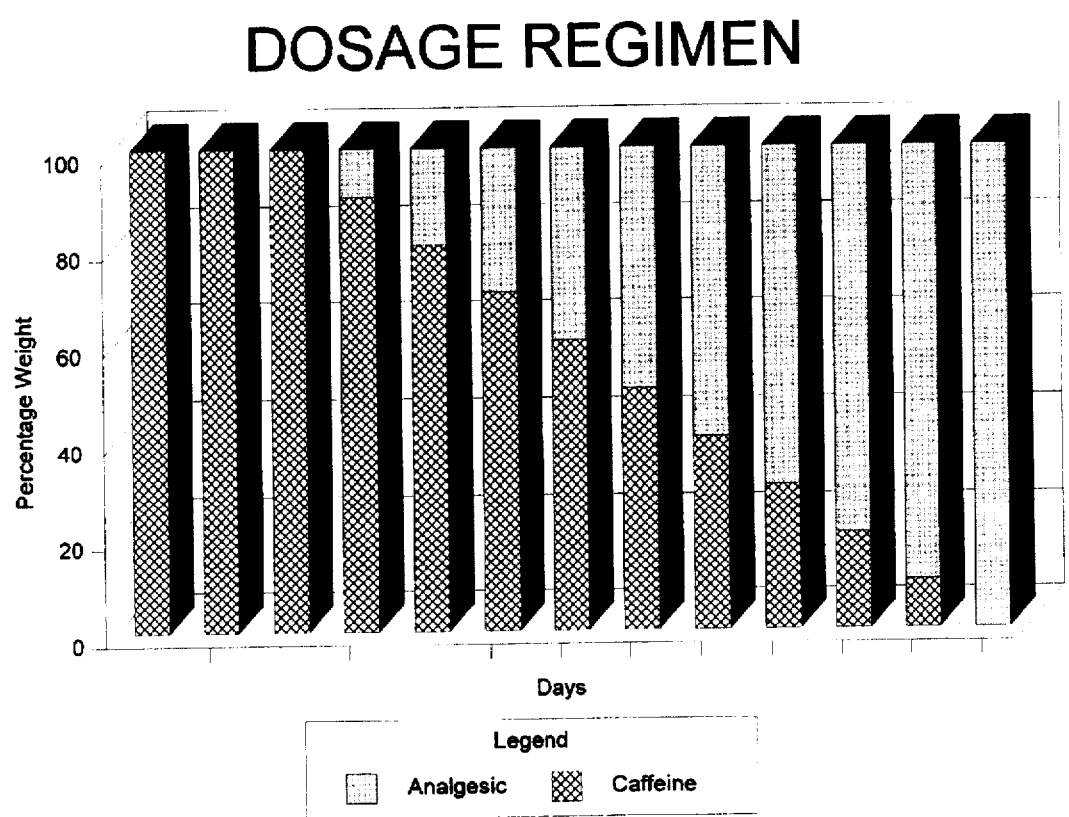
FIG. 2 depicts another embodiment of the system employing a dosage regimen of dosage units with proportions different from those depicted in FIG. 1.
Figure 3:
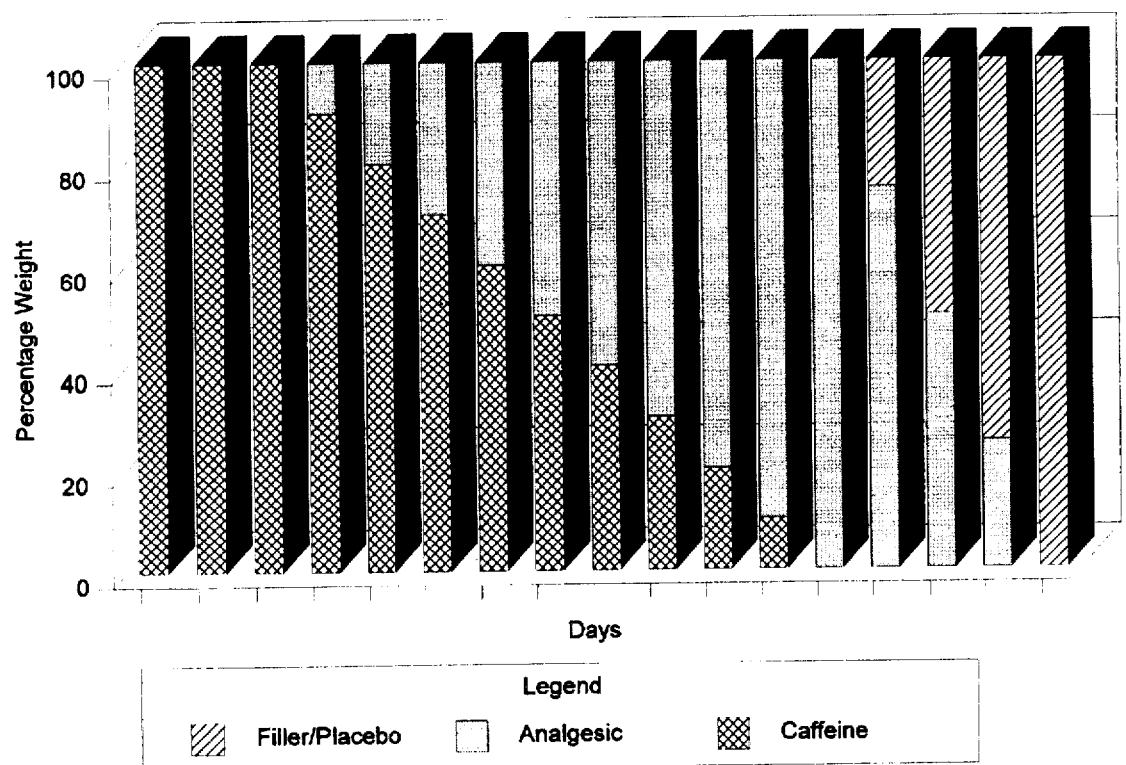
FIG. 3 depicts yet another regime for use in one embodiment of the caffeine withdrawal system.

Because withdrawal from caffeine dependency results in headaches, migraines, fatigue, and depression, the present invention contemplates incorporating into the dosage unit a quantity of an analgesic to relieve the pain associated with the physiological effects of caffeine withdrawal. As shown in FIGS. 1–6, as the quantity of caffeine is decreased, there is a corresponding increase in the amount of the analgesic to counteract the accompanying headaches associated with caffeine withdrawal. In this way, the introduction of an increased amount of the analgesic provides relief from symptomatic headaches. It also provides further psychological encouragement to the person by relieving or blocking the pain associated with caffeine withdrawal and thereby further encouraging the person to continue with the caffeine detoxification regimen. An alternative dosage regimen is shown in FIG. 3, in which caffeine intake is reduced to zero. The analgesic intake is not terminated, but is tapered off after the intake of caffeine has ceased to ensure a painless tail-off of caffeine. Again, the person is benefitted both physiologically by preventing or blocking any residual headaches and psychologically by transitioning the person off of caffeine and analgesic altogether in a painless way.

The preferred embodiment contemplates the combined composition of caffeine and analgesic in a solid tablet dosage form. However, semi-solid or liquid dosage forms could also be used. Other commonly known techniques for ingesting the medicament such as suspensions, liquids, powders, pills, capsules, suppositories, or the like could be used.

An optional, yet additional, component of a preferred caffeine withdrawal regimen would include a series of dosage units comprised merely of a placebo. As shown in FIGS. 3–6, at or near the end of caffeine withdrawal regimens contemplated by this invention, a series of dosage units could be continued incorporating no caffeine or analgesic. This additional series of dosage units would provide additional psychological assistance to the person withdrawing from caffeine dependency. In support thereof, numerous studies have shown that in some cases, placebo dosages have provided sufficient psychological advantage to assist persons following a medicament regimen. As shown in FIGS. 3–6, the placebo could be administered in the same form, size, and weight as the earlier combined dosage of caffeine and analgesic.

A preferred packaging of any of the embodiments described above contemplates the use of a push-through or punch-out card. That is, the preformulated, predetermined dosage units or tablets are presented to the user in a punch-out card in a preordered arrangement directing the user to punch out the proper tablet for each day of the dosage regimen. In this way, the user is certain to receive the appropriate tablet each day throughout the dosage regimen.

EXAMPLE 1

A person having a caffeine dependency due to regular medication of 150 milligrams of caffeine per day was provided a caffeine withdrawal dosage regimen over a ten (10) day period. Over the course of this dosage regimen, the caffeine quantity was decreased from 150 milligrams to 0 milligrams and over the same period of time, an increasing amount of Ibuprofen® was administered to counteract the side effects of caffeine withdrawal. The person experienced little or no headaches or other side effects of caffeine detoxification or withdrawal. FIG. 1.

EXAMPLE 2

A caffeine withdrawal dosage regimen is used to first deliver for one or more days the same amount or an increased amount of caffeine to the person. Thereafter, a combination of dosage units incorporating decreasing amounts of caffeine and increasing amounts of analgesic are administered to the person. Thereby, over a duration of about thirteen (13) days, the person's physiological demand for caffeine is withdrawn while at the same time an increasing amount of analgesic is received by the person to counteract any symptoms of caffeine withdrawal. At the end of this dosage regimen, the intake of caffeine is reduced to 0 milligrams. As a result, the person's caffeine dependency is removed and through the assistance of an analgesic the person has not suffered the side effects of caffeine withdrawal. FIG. 2.

EXAMPLE 3

A caffeine withdrawal dosage regimen is used to first deliver for one or more days the same amount or an increased amount of caffeine to the person. Thereafter, a combination of dosage units incorporating decreasing amounts of caffeine and increasing amounts of analgesic are administered to the person. Thereby, over a duration of about seventeen (17) days, the person's physiological demand for caffeine is reduced or eliminated while at the same time an increasing amount of analgesic is received by the person to counteract any symptoms of caffeine withdrawal. At the end of this dosage regimen, the intake of caffeine is reduced to 0 milligrams.

Thereafter, analgesic is continued to be administered for one or more days to counteract any residual headaches or other side effects. As a result, the person's caffeine dependency is removed and through the assistance of an analgesic the person has not suffered the side effects of caffeine withdrawal. Also FIG. 2.

EXAMPLE 4

A caffeine withdrawal dosage regimen is used to first deliver for one or more days the same amount or an increased amount of caffeine to the person. Thereafter, a combination of dosage units incorporating decreasing amounts of caffeine and increasing amounts of analgesic are administered to the person. Thereby, over a duration of about seventeen (17) days, the person's physiological demand for caffeine is withdrawn while at the same time an increasing amount of analgesic is received by the person to counteract any symptoms of caffeine withdrawal. At the end of this dosage regimen, the intake of caffeine is reduced to 0 milligrams. Thereafter, dosages of analgesic are administered in decreasing amounts for a number of days to counteract any residual headaches or other side effects of caffeine withdrawal. As a result, the person's caffeine dependency is removed and through the assistance of an analgesic the person has not suffered the side effects of caffeine withdrawal. FIG. 3.

EXAMPLE 5

Figure 4:
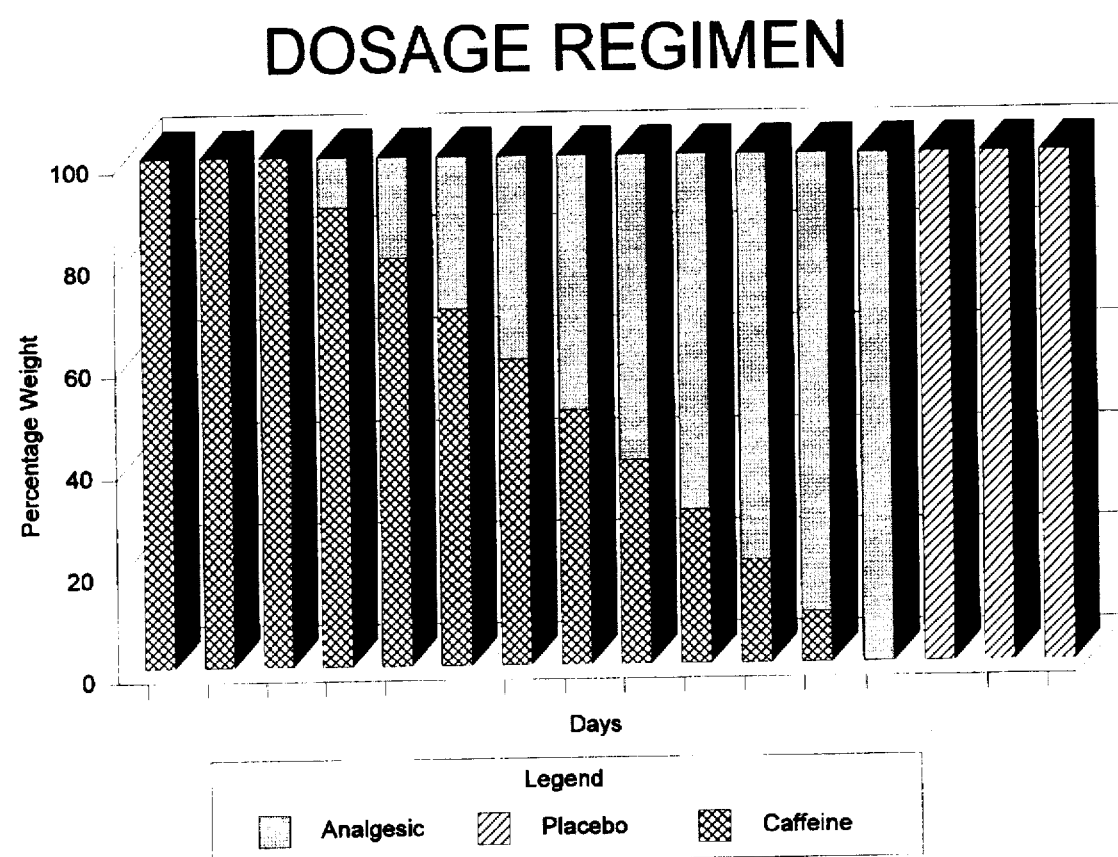
FIG. 4 depicts an embodiment of the system for caffeine withdrawal employing a regimen of dosage units varying in proportion and composition to those depicted in FIGS. 1–3.

A caffeine withdrawal dosage regimen is used to first deliver for one or more days the same amount or an increased amount of caffeine to the person. Thereafter, a combination of dosage units incorporating decreasing amounts of caffeine and increasing amounts of analgesic are administered to the person. Thereby, over a duration of about sixteen (16) days, the person's physiological demand for caffeine is withdrawn while at the same time an increasing amount of analgesic is received by the person to counteract any symptoms of caffeine withdrawal. At the end of this dosage regimen, the intake of caffeine is reduced to 0 milligrams. Thereafter, the person receives a placebo for one or more days. As a result, the person's caffeine dependency is removed and through the assistance of an analgesic the person has not suffered the side effects of caffeine withdrawal. FIG. 4.

EXAMPLE 6

Figure 5:
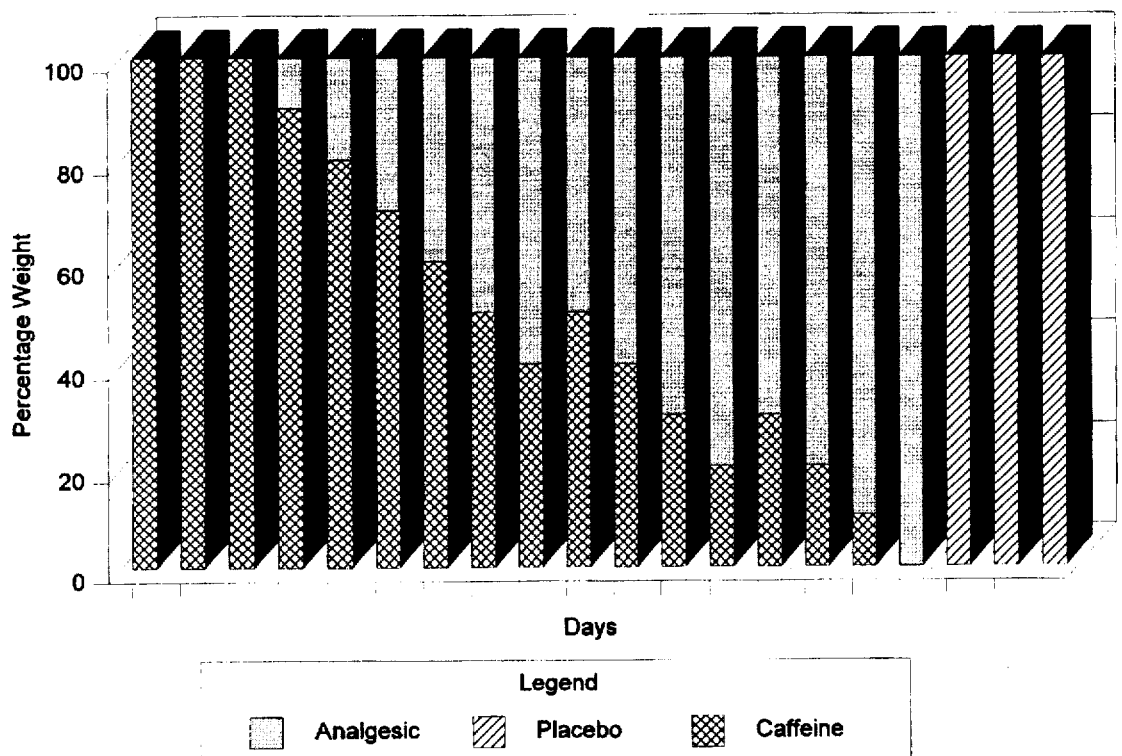
FIG. 5 depicts another embodiment of the system for caffeine withdrawal employing a regimen of dosage units composed of proportions of constituents different from those depicted in FIG. 4.

A caffeine withdrawal dosage regimen is used to first deliver for one or more days the same amount or an increased amount of caffeine to the person. Thereafter, a combination of dosage units incorporating decreasing amounts of caffeine and increasing amounts of analgesic are administered to the person. Thereby, over a duration of about twenty (20) days, the person's physiological demand for caffeine is withdrawn while at the same time an increasing amount of analgesic is received by the person to counteract any symptoms of caffeine withdrawal. At the end of this dosage regimen, the intake of caffeine is reduced to 0 milligrams. Thereafter, the person receives a placebo for a number of days. As a result, the person's caffeine dependency is removed and through the assistance of an analgesic the person has not suffered the side effects of caffeine withdrawal. While this dosage regimen mimics Examples 1–5, at some interval while the quantity of caffeine is being decreased, it is helpful to the person to have an intermittent increase of caffeine and thereafter a subsequent continuation of a decreasing quantity of caffeine until the quantity of caffeine is eliminated. In this way, the person's dependency for caffeine is removed while at the same time the person does not experience the headaches and other side effects of caffeine withdrawal with the assistance of an analgesic. FIG. 5.

It will be appreciated that the present invention may be embodied in several regimens in addition to those specifically set forth in the preceding examples. For example, one regimen could utilize a "plateau" technique wherein the ratio of caffeine and analgesic are maintained for several days to allow the patient to become accustomed to the lower level of caffeine before the amount of caffeine is decreased and the amount of analgesic increased. The process would then be repeated bringing the user to a lower level of caffine over several days and then administering a second plateau wherein the ratio of caffine and analgesic are maintained for several days.

EXAMPLE 7

Figure 6:
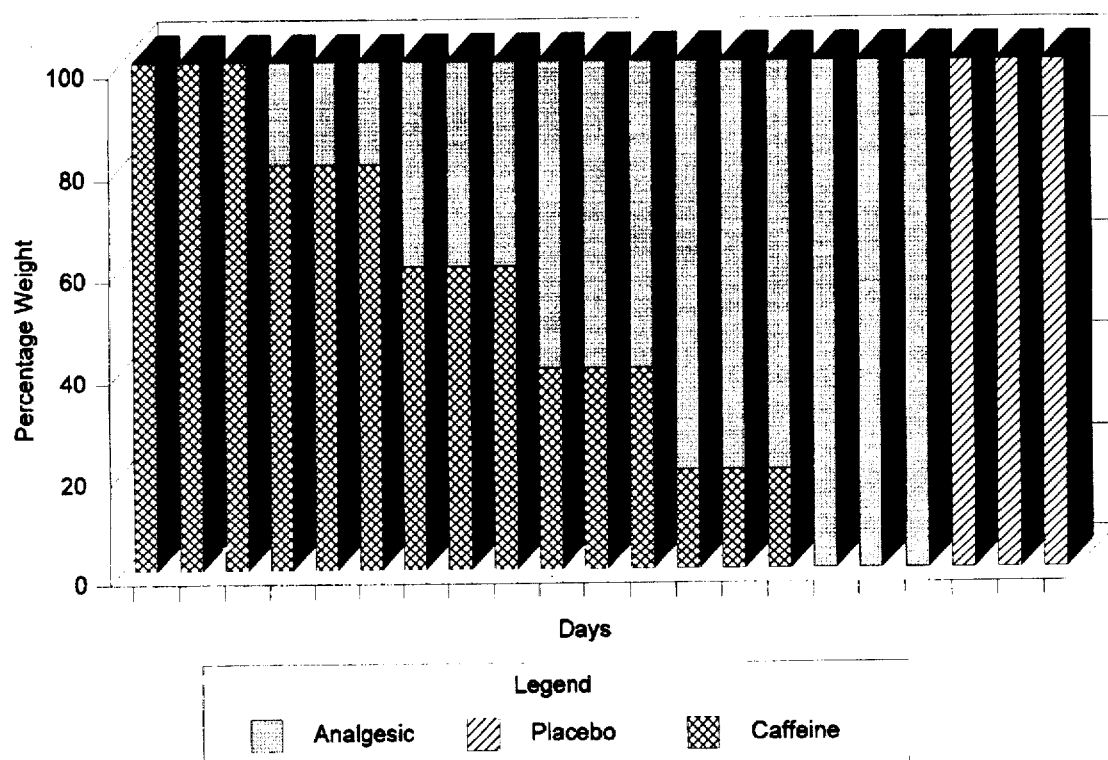
FIG. 6 depicts still another dosage regimen of another embodiment of a caffeine withdrawal system.

A caffeine withdrawal dosage regimen is used to first deliver for one or more days the same amount or an increased amount of caffeine to the person. Thereafter, a combination of dosage units incorporating a lesser amount of caffeine an amount of analgesic are administered to the person for one or more days such that for one or more days the person receives the same or a plateaued ratio of caffeine and analgesic. Thereafter, a combination of dosage units incorporating a still lesser amount of caffeine and a greater amount of analgesic are administered to the person for one or more days such that the person receives another plateaued ratio of caffeine and analgesic. FIG. 6. After a series of plateaued administrations, the person's caffeine dependency is removed and through the assistance of an analgesic the person has not suffered the side effects of caffeine withdrawal.

It will be appreciated that the duration in days of any of the above-described dosage regimens may be shortened or lengthened depending upon the amount of decrease of caffeine from level to level. The decrease in FIGS. 1–5 represents a 10% decrease in caffeine from level to level. FIG. 6 represents a 20% decrease from level to level. As a result, the duration of any dosage regimen may be shortened or lengthened depending upon the selected percentage decrease in caffeine. For example, the dosage regimen of FIGS. 3 and 4 could be shortened by five (5) days if the decrease in caffeine quantity occurred at 20% rather than 10% levels.

The present invention may be embodied in other specific forms without departing from its spirit or essential characteristics. For example, while Examples 1–7 describe initial amounts of analgesic as low, the present invention contemplates providing greater initial amounts of analgesic even a full dose through the dosage regimen. This could be accomplished by having the physical size of the dosage unit decreasing over time as less caffeine is administered to the patient or by keeping the physical size of the dosage unit the same by using a filter whose quantity is increased over time as the amount of caffeine being administered decreases. In either case, the psychologic benefits of the present invention are maintained as the patient's body acclimate to reduced levels of caffeine. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for effecting withdrawal from caffeine dependency comprising a regimen of dosage units, each dosage unit containing a quantity of caffeine and a quantity of analgesic such that at least one or more dosage units contain a higher percentage weight of caffeine than analgesic and such that at least one or more dosage units contain a higher percentage weight of analgesic than caffeine wherein the dosage units administered contain a progressively decreasing caffeine analgesic ratio over a set period.

2. A system defined in claim 1, further comprising at least one more dosage unit comprising caffeine only.

3. A system as defined in claim 1, further comprising at least one more dosage unit comprising analgesic only.

4. A system as defined in claim 1, further comprising at least one more dosage unit comprising a placebo.

5. A system as recited in claim 1, wherein the dosage units are contained in a stiff card having openings formed therein and being covered by a frangible membrane, the individual dosage units prearranged in a sequence in the openings in the stiff card such that a user may push the dosage unit through the frangible membrane to release the dosage unit from the card.

6. A system as recited in claim 5, wherein the dosage units are prearranged in a sequence wherein the first dosage unit in the sequence has a high caffeine/analgesic ratio and the last dosage unit in the sequence has a low caffeine/analgesic ratio.

7. A method of treatment for effecting a withdrawal from caffeine dependency and counteracting symptomatic side effects of headaches, depression, fatigue and general body discomfort comprising the following steps:

a) obtaining a plurality of dosage units comprising at least one dosage unit which contains caffeine and an analgesic wherein the percentage weight of caffeine is greater than the percentage weight of analgesic, and at least one dosage unit containing caffeine and an analgesic in which the percentage weight of analgesic is greater than the percentage weight of caffeine;

b) administering to a person one or more dosage units comprising caffeine and analgesic in which the percentage weight of caffeine is greater than the percentage weight of analgesic; and c) thereafter, administering one or more dosage units comprising caffeine and analgesic to the person wherein the percentage weight of analgesic is greater than the percentage weight of caffeine.

8. A method of effecting withdrawal from caffeine dependency as defined in claim 7, wherein the dosage units comprise caffeine and analgesic, wherein the percentage weight of caffeine is greater than the percentage weight of analgesic, and wherein the dosage unit is formulated such that a first unit dose administered to the person contains at least the level of caffeine to which the person has been dependent and wherein the last dosage unit has both caffeine and analgesic.

9. A method of effecting withdrawal from caffeine dependency as defined in claim 7, wherein the dosage unit comprises caffeine and analgesic, wherein the percentage of weight of caffeine is greater than the percentage weight of analgesic and is formulated such that a first unit dose administered to the person contains at least the level of caffeine to which the person has been dependent and wherein the last dosage unit administered has no caffeine.

10. A method as recited in claim 7, wherein the dosage units administered contain a continually gradually decreasing caffeine analgesic ratio for a set period, dosage units then containing a caffeine/analgesic ratio which is constant for a set period.

11. A method as recited in claim 10, further comprising the administration of dosage units having a gradually decreasing caffeine/analgesic ratio for a second set period, followed by the administration of a plateau level of dosage units having a constant caffeine/analgesic ratio.

12. A method of treatment for effecting a withdrawal from caffeine dependency and counteracting symptomatic side effects of headaches, depression, fatigue and general body discomfort comprising the following steps:

a. obtaining a plurality of dosage units comprising at least one dosage unit which contains caffeine and an analgesic wherein the percentage weight of caffeine is greater than the percentage weight of analgesic, and at least one dosage unit containing caffeine and an analgesic in which the percentage weight of analgesic is greater than the percentage weight of caffeine;

b. administering to a person one or more dosage units comprising caffeine and analgesic in which the percentage weight of caffeine is greater than the percentage weight of analgesic; and c. thereafter, administering one or more dosage units comprising caffeine and analgesic to the person wherein the percentage weight of analgesic is greater than the percentage weight of caffeine, and wherein the dosage units administered contain a continually gradually decreasing caffeine analgesic ratio for a set period, dosage units then containing a caffeine/analgesic ratio which is constant for a set period.

13. A method as recited in claim 12, further comprising the administration of dosage units having a gradually decreasing caffeine/analgesic ratio for a second set period, followed by the administration of a plateau level of dosage units having a constant caffeine/analgesic ratio.

* * * * *